US012544259B2

(12) United States Patent
Wu

(10) Patent No.: US 12,544,259 B2
(45) Date of Patent: Feb. 10, 2026

(54) SURGICAL IMPLANT DELIVERY WITH DUAL MODE DRIVE

(71) Applicant: Alcon Inc., Fribourg (CH)

(72) Inventor: Yinghui Wu, Cedar Hill, TX (US)

( * ) Notice: Subject to any disclaimer, the term of this patent is extended or adjusted under 35 U.S.C. 154(b) by 441 days.

(21) Appl. No.: 18/182,573

(22) Filed: Mar. 13, 2023

(65) Prior Publication Data

US 2023/0301833 A1 Sep. 28, 2023

Related U.S. Application Data

(60) Provisional application No. 63/269,840, filed on Mar. 24, 2022.

(51) Int. Cl.
*A61F 9/007* (2006.01)
*A61F 2/02* (2006.01)

(52) U.S. Cl.
CPC ................ *A61F 9/007* (2013.01); *A61F 2/02* (2013.01)

(58) Field of Classification Search
None
See application file for complete search history.

(56) References Cited

U.S. PATENT DOCUMENTS 7,156,854 B2 1/2007 Brown et al.
8,105,332 B2 1/2012 Downer et al.
8,377,076 B2 2/2013 Downer et al.
10,568,735 B2 2/2020 Brown et al.
10,588,780 B2 3/2020 Noy et al.
11,433,186 B2 * 9/2022 Ulla .................. A61M 5/31575
2006/0085013 A1 * 4/2006 Dusek ................... A61F 2/1664 606/107
2012/0022548 A1 * 1/2012 Zacharias ............. A61F 2/1672 606/107
2020/0015959 A1 1/2020 Wensrich et al.
2020/0197166 A1 6/2020 Wu et al.
2023/0062291 A1 * 3/2023 Romoda ................ A61B 17/34

FOREIGN PATENT DOCUMENTS

WO 2022048766 A1 3/2022

OTHER PUBLICATIONS

HOYA Vivinex MultiSert, Internet, Jan. 24, 2021, 2 pages, https://eifu.hoyasurgicaloptics.com/down/uploads/2021-01-24-hsoe-xc1-sp-xy1-sp-ds-en_818_1614266480.pdf, Chromos, Singapore.
International Search Report, PCT/B2023/052409, Jun. 12, 2023.

* cited by examiner

*Primary Examiner* — Michael T. Holtzclaw

(57) ABSTRACT

An apparatus for eye surgery. Some embodiments may comprise a housing, a bore through the housing, and a push rod at least partially disposed in the bore. The push rod may be operable to move between three rod positions within the bore. A plunger key may be coupled to the housing and operable to move between three key positions. In the first key position, the plunger key may prevent the push rod from moving from a first rod position. In the second key position, the plunger key may allow the push rod to slide through the bore from the first rod position to a second rod position. In the second key position, the plunger key may also allow the push rod to be rotated to advance to a third rod position. In the third key position, the plunger key may allow the push rod to slide through the bore from the second rod position to the third rod position.

15 Claims, 14 Drawing Sheets

SURGICAL IMPLANT DELIVERY WITH DUAL MODE DRIVE

TECHNICAL FIELD

The invention set forth in the appended claims relates generally to eye surgery. More particularly, but without limitation, the claimed subject matter relates to systems, apparatuses, and methods for inserting an implant into an eye.

BACKGROUND

The human eye can suffer a number of maladies causing mild deterioration to complete loss of vision. While contact lenses and eyeglasses can compensate for some ailments, ophthalmic surgery may be required for others. In some instances, implants may be beneficial or desirable. For example, an intraocular lens may replace a clouded natural lens within an eye to improve vision.

While the benefits of intraocular lenses and other implants are known, improvements to delivery systems, components, and processes continue to improve outcomes and benefit patients.

BRIEF SUMMARY

New and useful systems, apparatuses, and methods for eye surgery are set forth in the appended claims. Illustrative embodiments are also provided to enable a person skilled in the art to make and use the claimed subject matter.

Some embodiments may provide an apparatus for eye surgery, which may integrate two delivery modes into a single pre-loaded delivery system. For example, the apparatus may provide both single-handed push and two-handed push and twist options so that a surgeon may choose a delivery mode based on preference or circumstances.

In more particular examples, the apparatus may have a plunger key with multiple positions. In a first position, the plunger key may lock a plunger in place, which may be advantageous for shipping and storage, for example. In a second position, the plunger may be released for axial sliding to a dwell position. From the dwell position, the plunger key may be left in the second position for a twist delivery or moved to a third position. In the third position, the plunger may be released for a push delivery from the dwell position. In some examples, the plunger key may be coupled to a housing, and rotation may be substantially restricted or prevented while moving axially between positions.

More generally, some embodiments of an apparatus for eye surgery may comprise a housing, a bore through the housing, and a push rod at least partially disposed in the bore. The push rod may be operable to move from a first rod position to a second rod position and a third rod position within the bore. The apparatus may further comprise a plunger key, which may be coupled to the housing and operable to move between a first key position, a second key position, and a third key position. In some examples, the plunger key may move axially between positions, and may be prohibited from rotating as it moves between positions. In the first key position, the plunger key may lock the push rod, which can prevent the push rod from moving from the first rod position. In the second key position, the plunger key may allow the push rod to slide through the bore from the first rod position to the second rod position. In the second key position, the plunger key may also allow the push rod to be rotated to the third rod position. In the third key position, the plunger key may allow the push rod to slide through the bore from the second rod position to the third rod position.

In more particular embodiments, a portion of the push rod may comprise threads, and the plunger key may comprise one or more thread tracks configured to mate with the threads of the push rod so that the push rod may be rotated to advance from the second rod position to the third rod position if the plunger key is in the second key position. In some embodiments, the push rod may further comprise a slide track, and the plunger key may be configured to slidingly engage the slide track if the plunger key is in the second key position and the push rod is between the first rod position and the second rod position. The push rod may additionally or alternatively comprise a keyway configured to receive a portion of the plunger key in the first rod position and the first key position, whereby the push rod may be retained in the first rod position by the portion of the plunger key disposed in the keyway.

In more particular embodiments, a plunger key may comprise a shank, a tip coupled to one end of the shank, and one or more snap fittings coupled to the shank. The snap fittings may be configured to engage the key mount in each of the first key position, the second key position, and the third key position. The key mount may comprise a catch configured to engage the plunger key in each of the first key position, the second key position, and the third key position.

Additionally, or alternatively, some embodiments of an apparatus may further comprise a nozzle, an implant bay coupled to the nozzle, an implant disposed within the implant bay, and a plunger coupled to the push rod in the bore. The push rod may be configured to advance the plunger to advance the implant through the nozzle as the push rod moves to the third rod position.

In other example embodiments, an apparatus for eye surgery may comprise a housing, a key mount coupled to the housing, a bore through the housing, a plunger disposed in the bore, a push rod coupled to the plunger, and a plunger key. The key mount may comprise a key track and a catch, the push rod may comprise a keyway, a slide track, and threads. The plunger key may comprise a shank disposed within the key track, a tip coupled to one end of the shank, a snap fitting coupled to the shank, and a lug coupled to the snap fitting. The tip may have one or more thread tracks. The push rod may be operable to move from a first rod position to a second rod position and a third rod position within the bore. The shank may be operable to move the tip from a first key position to a second key position and a third key position. The lug may be configured to engage the catch in each of the first key position, the second key position, and the third key position. In the first key position, the tip may be disposed in the keyway. In the second key position, the tip may be configured to engage the slide track between the first rod position and the second rod position. In the second key position, the thread tracks may be configured to engage the threads between the second rod position and the third rod position.

In yet other examples, an apparatus may comprise a nozzle, an implant bay coupled to the nozzle, an implant disposed in the implant bay, a housing, and a bore through the housing. An actuator may comprise a plunger disposed within the bore and a push rod at least partially disposed in the bore. The push rod may be operable to move the plunger from a first plunger position to a second plunger position and a third plunger position within the bore. A plunger key may be coupled to the housing and operable to move between a first key position, a second key position, and a third key position. In the first key position, the plunger key may prevent the push rod from moving the plunger from the first plunger position. In the second key position, the plunger key may allow the push rod to slide the plunger through the bore from the first plunger position to the second plunger position and to rotate to move the plunger to the third plunger position to advance the implant from the implant bay through the nozzle. In the third key position, the plunger key may allow the push rod to slide the plunger through the bore from the second plunger position to the third plunger position to advance the implant from the implant bay through the nozzle.

Features, elements, and aspects described in the context of some embodiments may also be omitted, combined, or replaced by alternative features. Other features, objectives, advantages, and a preferred mode of making and using the claimed subject matter are described in greater detail below with reference to the accompanying drawings of illustrative embodiments.

BRIEF DESCRIPTION OF THE DRAWINGS

The accompanying drawings illustrate some objectives, advantages, and a preferred mode of making and using some embodiments of the claimed subject matter. Like reference numbers represent like parts in the examples.

DESCRIPTION OF EXAMPLE EMBODIMENTS

The following description of example embodiments provides information that enables a person skilled in the art to make and use the subject matter set forth in the appended claims, but it may omit certain details already well known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive an implant. However, as should be recognized by those skilled in the art, this frame of reference is merely a descriptive expedient rather than a strict prescription.

Figure 1:
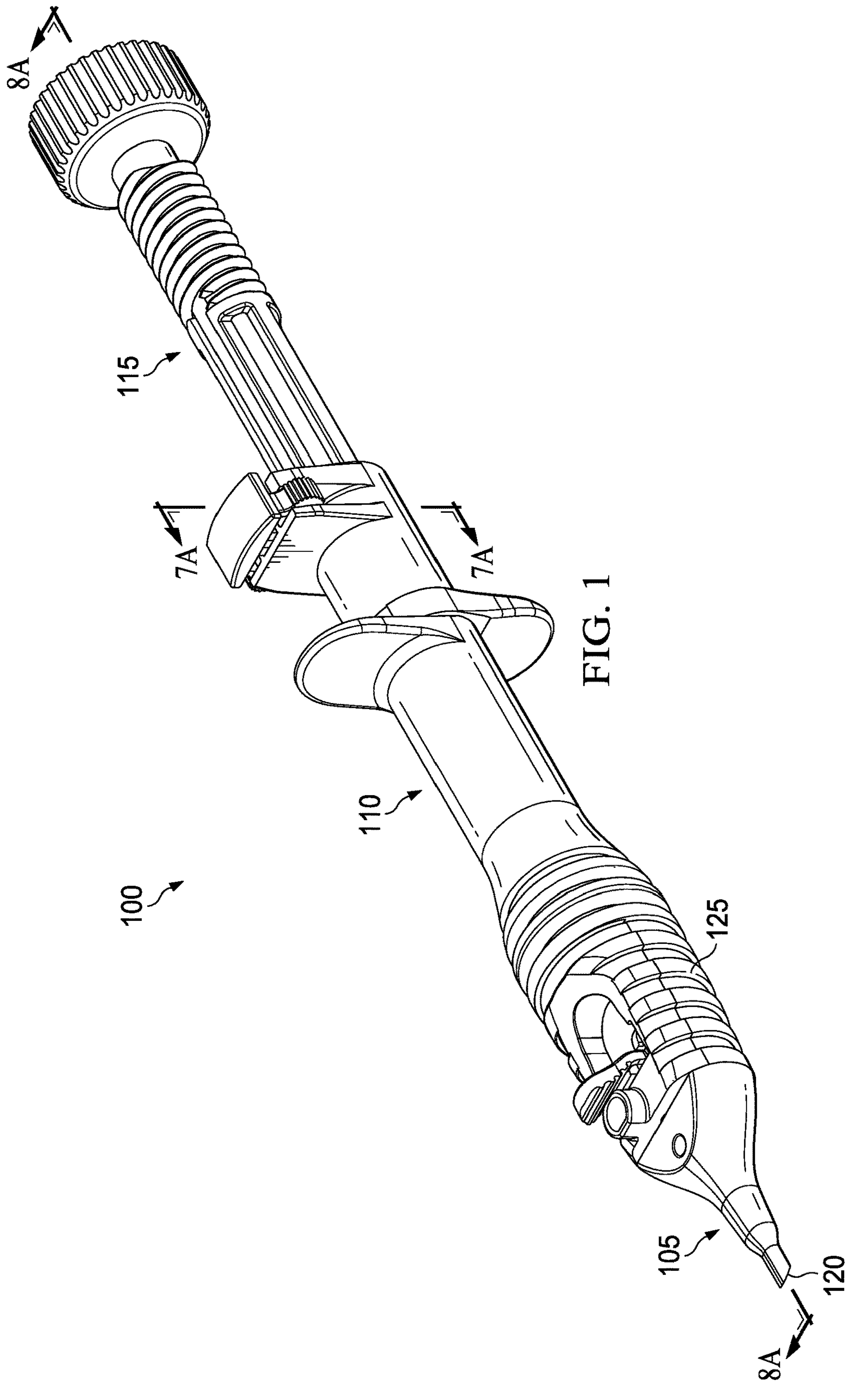
FIG. 1 is an auxiliary view of an example apparatus for delivering an implant into an eye.

FIG. 1 is an auxiliary view of an example of an apparatus 100 that can deliver an implant into an eye. In some embodiments, the apparatus 100 may comprise two or more modules, which can be configured to be coupled and decoupled as appropriate for storage, assembly, use, and disposal. As illustrated in FIG. 1, some embodiments of the apparatus 100 may include a nozzle 105, a housing 110 coupled to the nozzle 105, and an actuator 115 coupled to the housing 110.

The nozzle 105 generally comprises a tip 120 adapted for insertion through an incision into an eye. The size of the tip 120 may be adapted to surgical requirements and techniques as needed. For example, small incisions are generally preferable to reduce or minimize healing times. Incisions of less than 2 millimeters may be preferable in some instances, and the tip 120 of the nozzle 105 may have a width of less than 2 millimeters in some embodiments.

The housing 110 is generally configured to receive at least a portion of the actuator 115. The housing 110 may further comprise an implant bay 125, which generally represents a wide variety of apparatuses that are suitable for storing an implant prior to delivery into an eye. In some embodiments, the implant bay 125 may additionally or alternatively be configured to prepare an implant for delivery. For example, some embodiments of the implant bay 125 may be configured to be actuated by a surgeon or other operator to prepare an implant for delivery by subsequent action of the actuator 115. In some instances, the implant bay 125 may be configured to actively deform, elongate, extend, or otherwise manipulate features of the implant before the implant is advanced into the nozzle 105. For example, the implant bay 125 may be configured to fold, extend, or splay one or more features, such as haptics, of an intraocular lens.

The actuator 115 is generally configured to advance an implant from the implant bay 125 into the nozzle 105, and thereafter from the nozzle 105 through an incision and into an eye.

In general, components of the apparatus 100 may be coupled directly or indirectly. For example, the nozzle 105 may be directly coupled to the implant bay 125 and may be indirectly coupled to the actuator 115 through the implant bay 125. Coupling may include fluid, mechanical, thermal, electrical, or chemical coupling (such as a chemical bond), or some combination of coupling in some contexts. For example, implant bay 125 may be mechanically coupled to the actuator 115 and may be mechanically and fluidly coupled to the nozzle 105. In some embodiments, components may also be coupled by virtue of physical proximity, being integral to a single structure, or being formed from the same piece of material.

Figure 2:
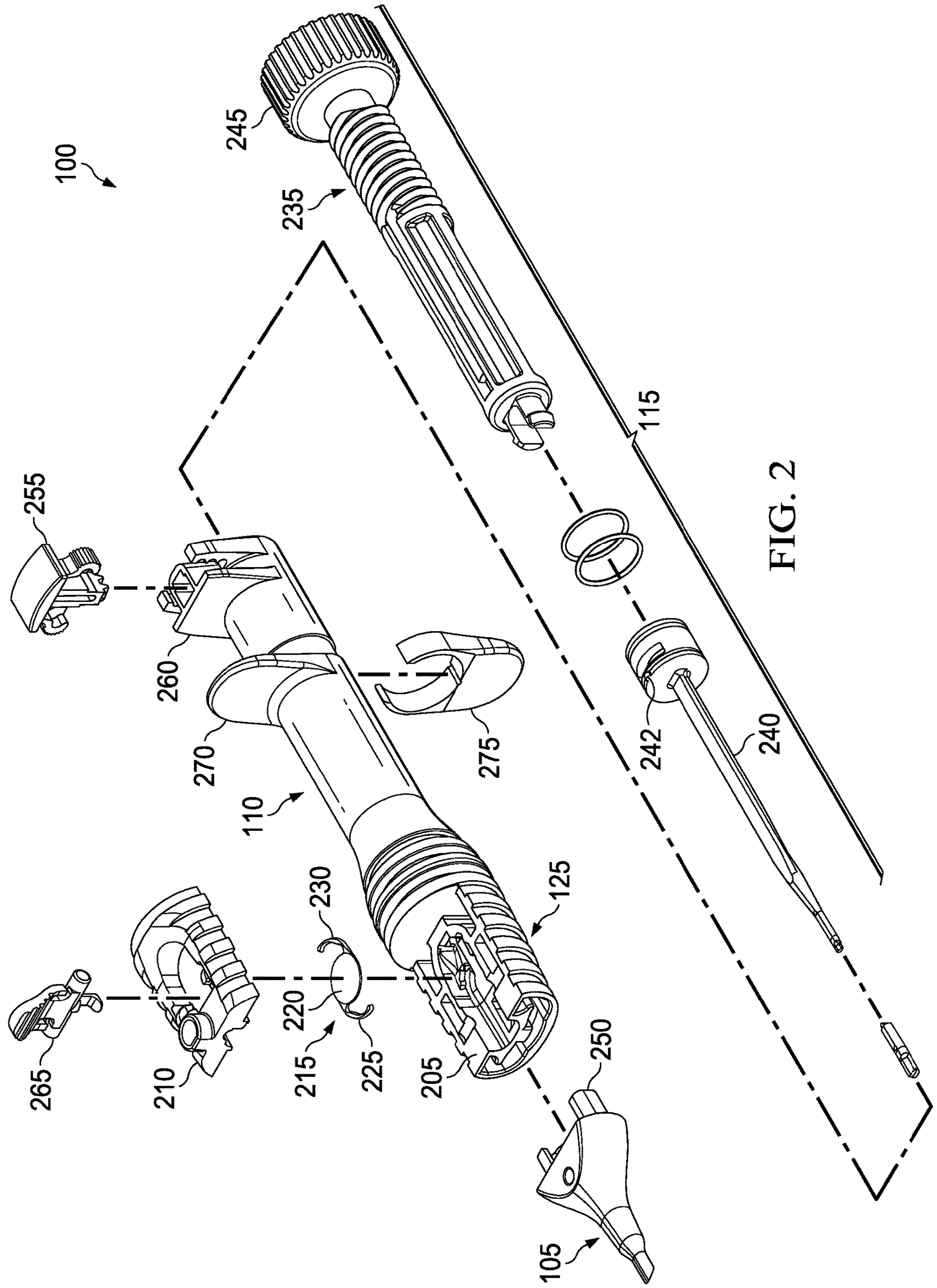
FIG. 2 is an exploded view of the apparatus of FIG. 1.

FIG. 2 is an exploded view of the apparatus 100 of FIG. 1, illustrating additional details that may be associated with some embodiments. For example, the implant bay 125 of FIG. 2 comprises a base 205 and a cap 210, which may be coupled to the base 205.

An implant 215 may be disposed between the base 205 and the cap 210. In the example of FIG. 2, the implant 215 is an intraocular lens having an optic body 220. In some examples, the optic body 220 may have a shape similar to that of a natural lens of an eye. Examples of suitable materials may include silicone, acrylic, and combinations of such suitable materials. The implant 215 may also comprise one or more features for positioning the optic body 220 within an eye, such as a leading haptic 225 and a trailing haptic 230. In the example of FIG. 2, the leading haptic 225 and the trailing haptic 230 extend from opposing sides of the optic body 220. In some instances, the implant 215 may be filled with a fluid, such as a fluid-filled accommodating intraocular lens.

As shown in the example of FIG. 2, some embodiments of the actuator 115 may comprise a push rod 235, a plunger 240 coupled to one end of the push rod 235, and a finger grip 245 coupled to the opposite end of the push rod 235. The plunger 240 may additionally comprise a lug 242.

The nozzle 105 of FIG. 2 comprises a bay interface 250, which can be coupled to the base 205.

Additionally, the apparatus of FIG. 2 may comprise a plunger key 255. In some examples, the plunger key 255 may be coupled to a key mount 260 on the housing 110.

FIG. 2 also illustrates an implant stop 265, a first finger flange 270, and a second finger flange 275, one or more of which may be associated with various examples of the apparatus 100.

Figure 3:
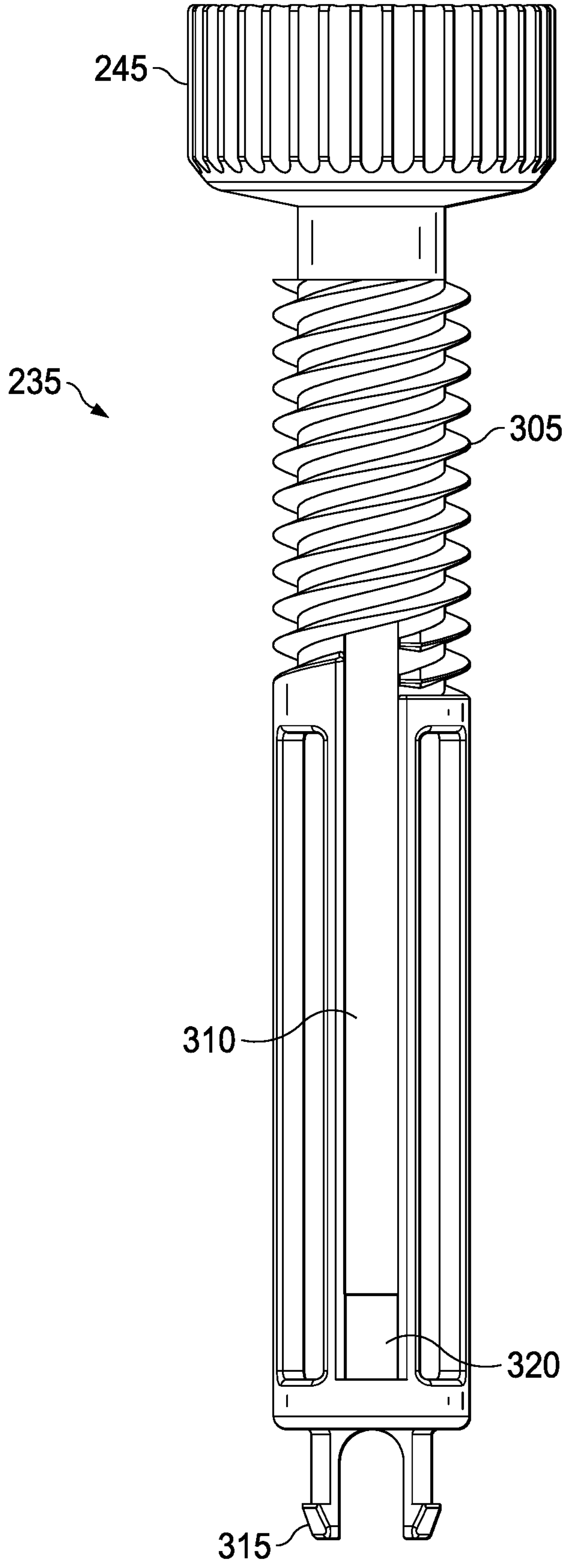
FIG. 3 is a top view of a push rod illustrated in the example of FIG. 2.

FIG. 3 is a top view of the push rod 235 of FIG. 2, illustrating additional details that may be associated with some embodiments. For example, as illustrated in FIG. 3, some embodiments of the push rod 235 may comprise threads 305. Some embodiments may additionally comprise a slide track 310, a plunger interface 315, or both. The plunger interface 315 may be disposed on an end opposite the finger grip 245, as shown in the example of FIG. 3. The slide track 310 may be a groove, channel, or similar feature in the push rod 235. Some embodiments may also comprise a keyway 320. As illustrated in the example of FIG. 3, the keyway 320 may be disposed near one end of the push rod 235. In more particular examples, the keyway 320 may be disposed adjacent to an end of the slide track 310.

Figure 4:
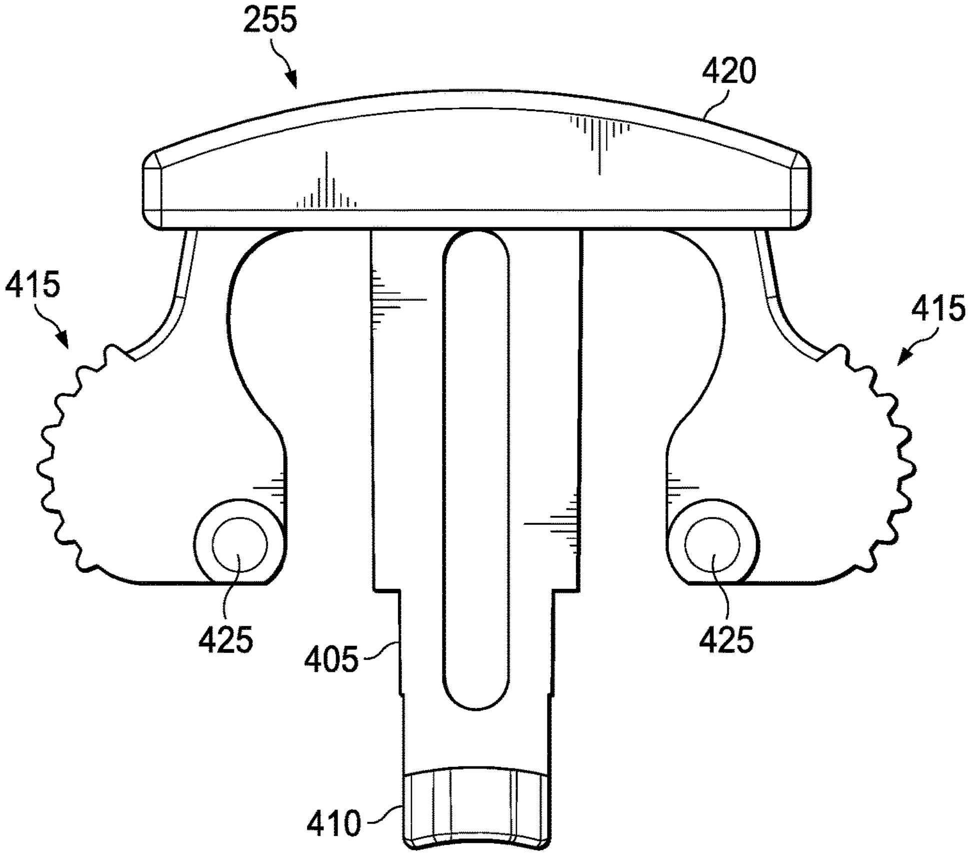
FIG. 4 is a rear view of a plunger key illustrated in the example of FIG. 2.

FIG. 4 is a rear view of the plunger key 255 of FIG. 2, illustrating additional details that may be associated with some embodiments. The plunger key 255 of FIG. 4 generally comprises a shank 405, a tip 410 coupled to one end of the shank 405, and one or more snap fittings 415 coupled to the shank 405. In the example of FIG. 4, the plunger key 255 comprises two of the snap fittings 415, each of which is indirectly coupled to the shank 405 through a crossbar 420. More particularly, each of the snap fittings 415 is coupled to opposite ends of the crossbar 420 of FIG. 4. As illustrated in the example of FIG. 4, the shank 405 is coupled to a central portion of the crossbar 420, and each of the snap fittings 415 may extend from the crossbar 420, generally parallel to the shank 405. In more particular examples, each of the snap fittings 415 may be cantilevered from the crossbar 420. Some embodiments of the plunger key 255 may further comprise one or more lugs 425. In the example of FIG. 4, the plunger key 255 comprises two of the lugs 425, each of which is coupled to one of the snap fittings 415.

Figure 5:
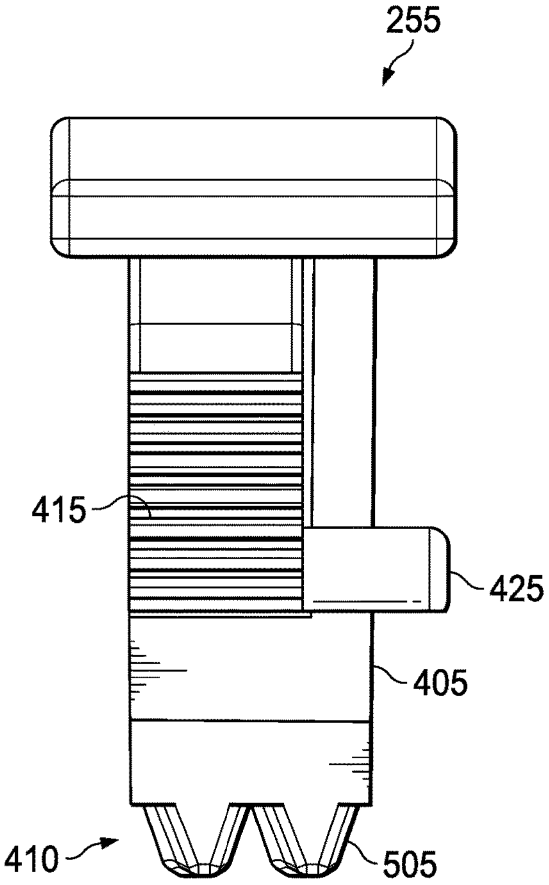
FIG. 5 is a side view of the plunger key of FIG. 4.

FIG. 5 is a side view of the plunger key 255 of FIG. 4, illustrating additional details that may be associated with some embodiments. For example, as illustrated in FIG. 5, the tip 410 may comprise thread tracks 505. The thread tracks 505 may be parallel in some examples. As also illustrated in FIG. 5, some embodiments of the lugs 425 may extend from the snap fittings 415. In the example of FIG. 5, the lugs 425 generally extend from the snap fittings 415 orthogonal to the shank 405.

Figure 6:
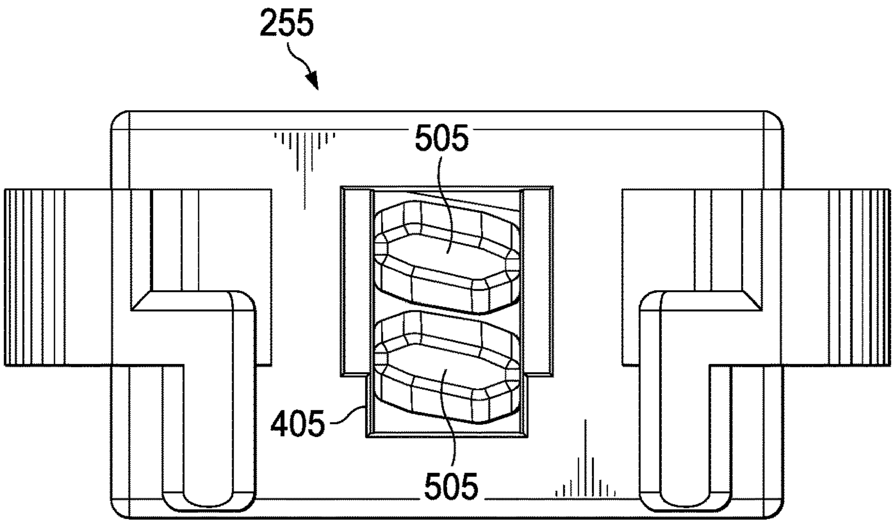
FIG. 6 is a bottom view of the plunger key of FIG. 4.

FIG. 6 is a bottom view of the plunger key 255 of FIG. 4, illustrating additional details that may be associated with some embodiments. As illustrated in FIG. 6, the thread tracks 505 may be disposed at an angle relative to the shank 405. In general, the thread tracks 505 may form a helical section.

Figure 7A:
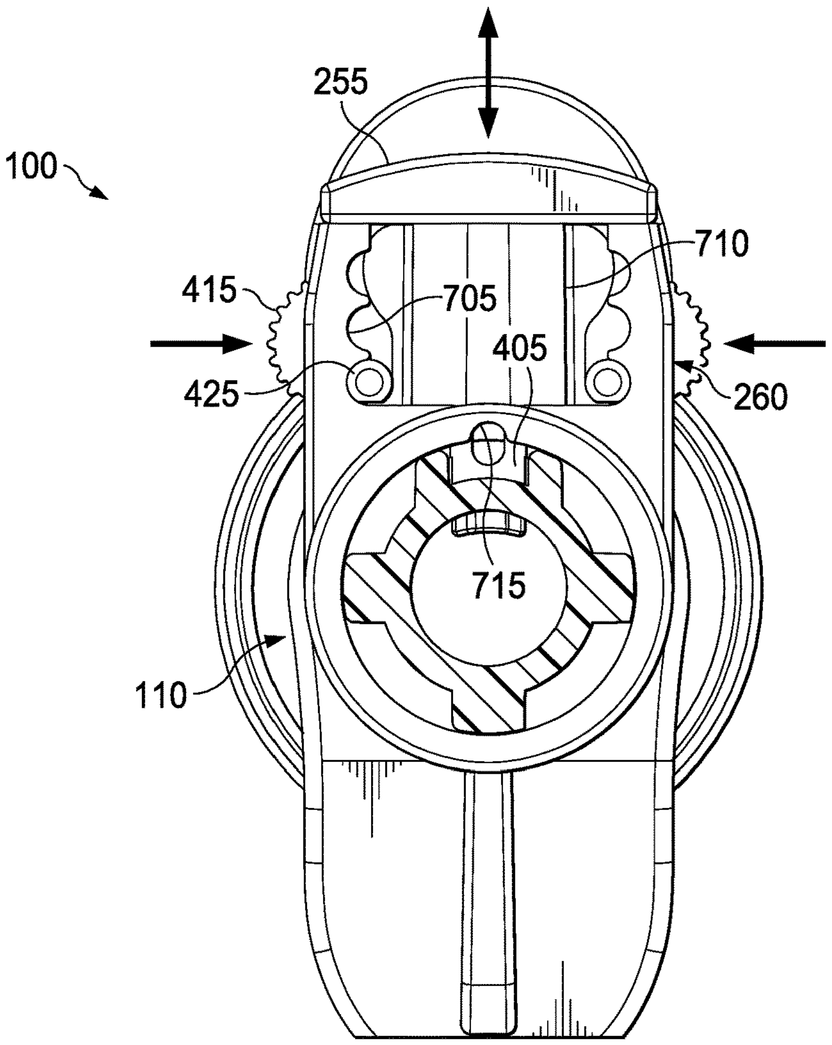
FIG. 7A, FIG. 7B, and FIG. 7C are rear section views of the apparatus of FIG. 1.
Figure 7C:
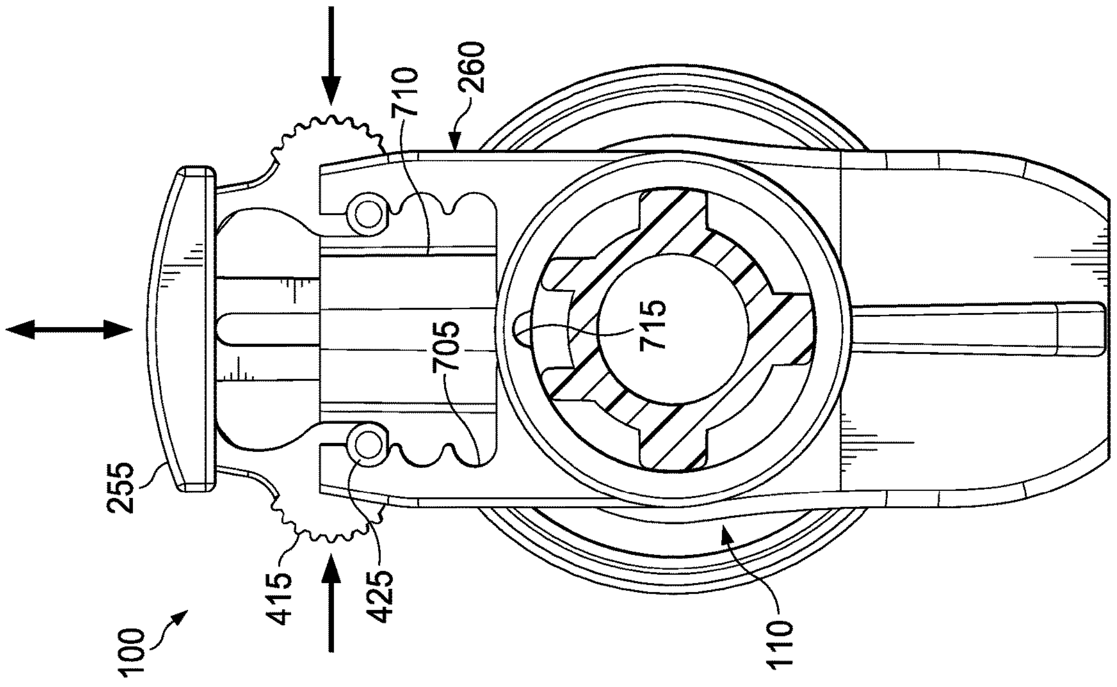
Figure 7B:
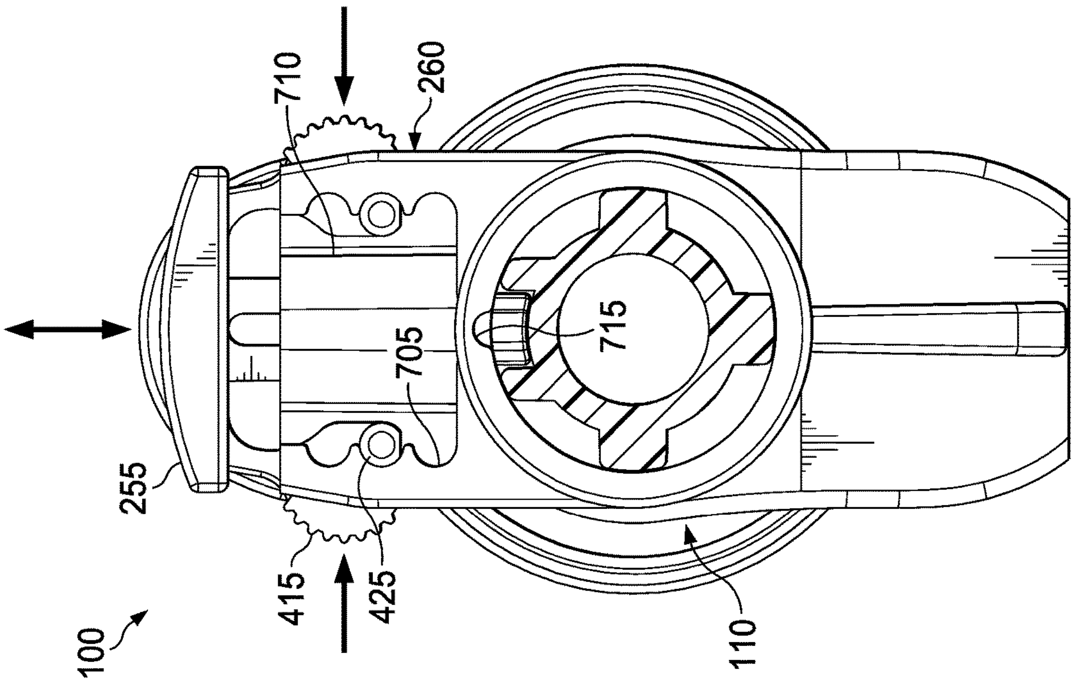

FIG. 7A, FIG. 7B, and FIG. 7C are section views of the apparatus 100 of FIG. 1, taken along section line 7-7. More particularly, FIG. 7A illustrates the plunger key 255 of FIG. 4 in a first position, FIG. 7B illustrates it in a second position, and FIG. 7C illustrates it in a third position. As illustrated in FIG. 7A, FIG. 7B, and Figure C, the key mount 260 may comprise a catch 705 and a key track 710. The catch 705 can engage the lugs 425 to retain the plunger key 255 in each of the positions. The snap fittings 415 may be pressed toward the shank 405 to release the lugs 425 from the catch 705 in each position and allow the shank 405 to move within the key track 710. In the example of FIGS. 7A-7C, the shank 405 can slide axially within the key track 710, and the key track 710 can substantially restrict or prevent rotation of the shank 405. Also illustrated in the example of FIGS. 7A-7C is a plunger track 715 in the housing 110.

Figure 8A:
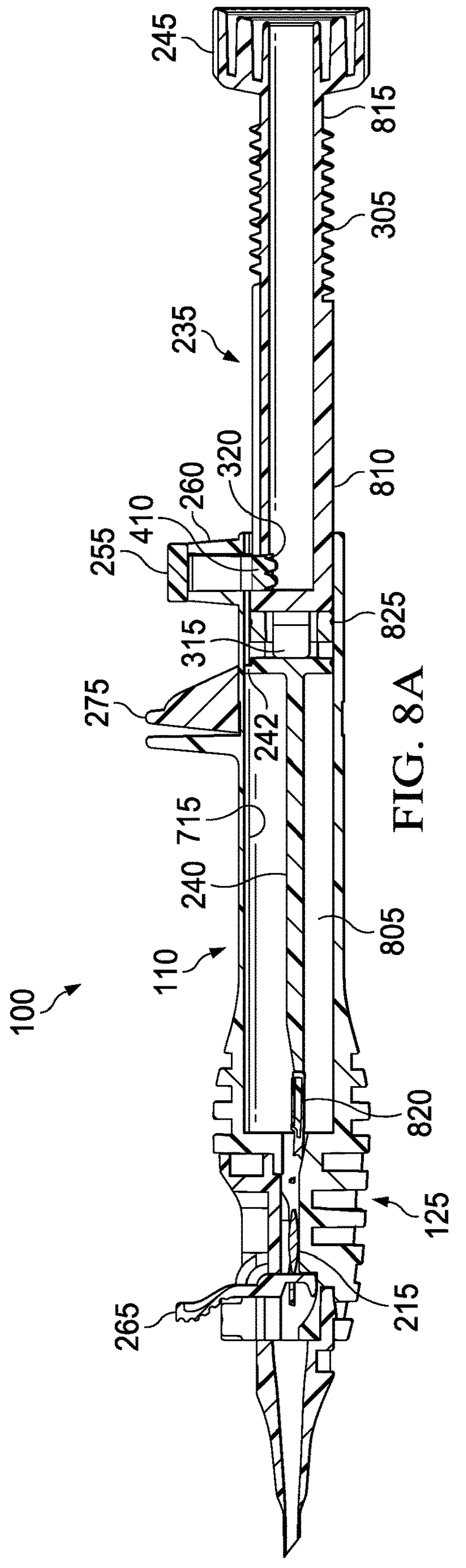
FIG. 8A-8E are side section views of the apparatus of FIG. 1 in different states.
Figure 8B:
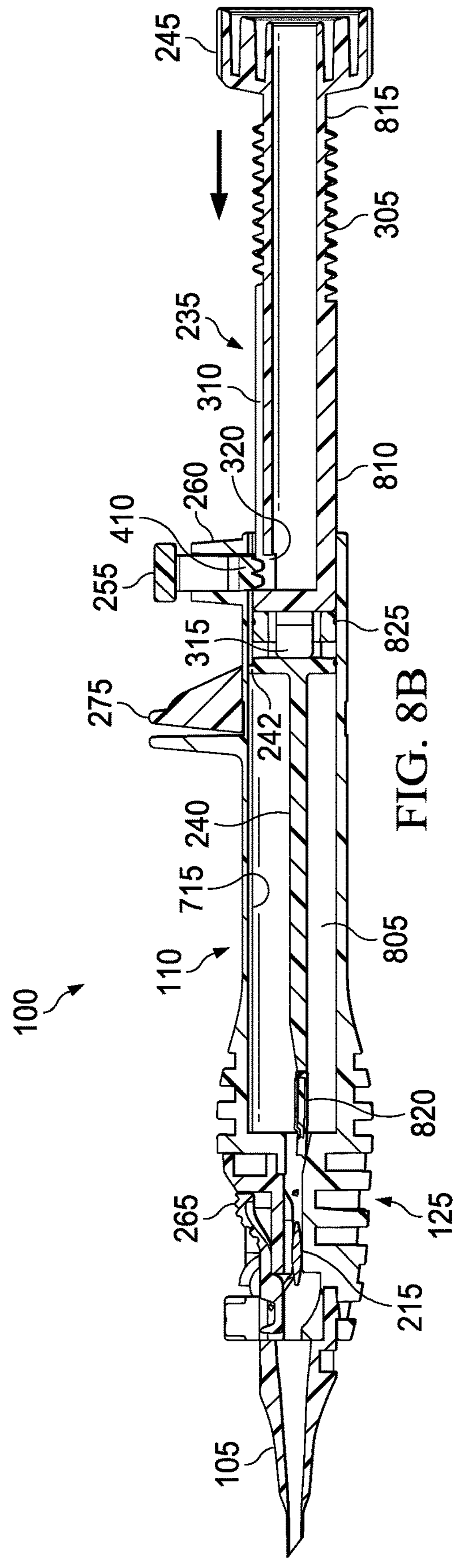
Figure 8C:
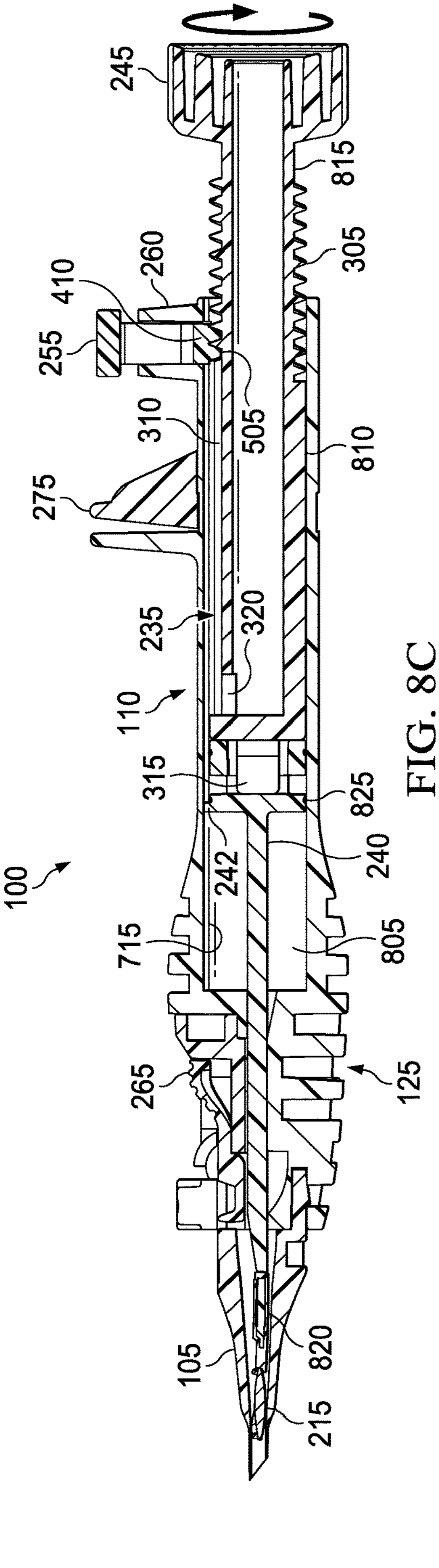

FIG. 8A-8E are section views taken along section line 8-8, illustrating additional details that may be associated with some embodiments of the apparatus 100 in different states. FIG. 8A, FIG. 8B, and FIG. 8C each generally illustrate an example of the apparatus 100 having the housing 110 of FIG. 2 and a bore 805 through the housing 110. The push rod 235 may be at least partially disposed in the bore 805. For example, the push rod 235 may have a first end 810 disposed within the bore 805. A second end 815 may extend from the bore 805, and the finger grip 245 may be coupled to the second end 815. The plunger 240 may also be disposed within the bore 805. Some embodiments of the plunger 240 may have a tip 820 and a head 825. The head 825 may be coupled to the push rod 235. In some examples, the head 825 may be coupled to the plunger interface 315, which can allow the push rod 325 to advance the plunger 240. In some embodiments, the plunger 240 may also be coupled to the housing 110 to control rotational movement of the plunger 240. For example, the lug 242 can engage the plunger track 715, which can allow the push rod 235 to advance the plunger 240 axially while preventing rotation of the plunger 240 within the bore 805. The plunger key 255 may be disposed within or otherwise coupled to the key mount 260.

In the example state of FIG. 8A, the implant 215 is disposed in the implant bay 125. In this state, the implant stop 265 may also be configured to prevent forward movement of the implant 215. FIG. 8A illustrates the apparatus 100 with the plunger key 255 in the first key position of FIG. 7A. In this position, the tip 410 of the plunger key 255 is disposed in the keyway 320, which can prevent movement of the push rod 235. This state may be advantageous for transporting and storing the apparatus 100, for example.

The example of FIG. 8B illustrates a second state of the apparatus 100 in which the implant stop 265 has been rotated from the first position of FIG. 8A to a second position that does not prevent forward movement of the implant 215. In this state, the implant 215 may be folded or otherwise manipulated to prepare it for advancement through the nozzle 105. The plunger key 255 has also been moved to a second key position, corresponding substantially to the position illustrated in FIG. 7B. In this second key position, the tip 410 of the plunger key 255 is removed from the keyway 320.

From the state illustrated in FIG. 8B, the push rod 235 may be advanced axially through the bore 805, and the tip 410 of the plunger key 255 may engage the slide track 310 to substantially prevent rotation of the push rod 235.

In the third state of the apparatus 100 illustrated in FIG. 8C, the implant 215 has been folded, and the push rod 235 and the plunger 240 have been advanced to a second position, thereby advancing the implant 215 from the implant bay 125 into the nozzle 105. In the example of FIG. 8C, the end of the slide track 310 is configured to be synchronized with the second position of the push rod 235 and the plunger 240. The end of the slide track 310 can also provide a hard stop to the push rod 235 at the second position. The push rod 235 of FIG. 8C has been advanced until the tip 410 of the plunger key 255 engages the threads 305 of the push rod 235. For example, the thread tracks 505 may comprise or consist essentially of a helical section adapted to mate with the threads 305. Significantly, the thread tracks 505 may be adapted to mate with threads having a wide variety of forms, thread angles, leads, and pitches, and starts. In this state, the tip 410 substantially prevents further advancement of the push rod 235 by axial loads.

In the state illustrated in FIG. 8C, the push rod 235 may be advanced by rotating the push rod 235. For example, the finger grip 245 may be rotated, causing the threads 305 to rotate relative to the thread tracks 505, which can convert the rotational motion of the push rod 235 to linear motion, thereby advancing the push rod 235.

Figure 8D:
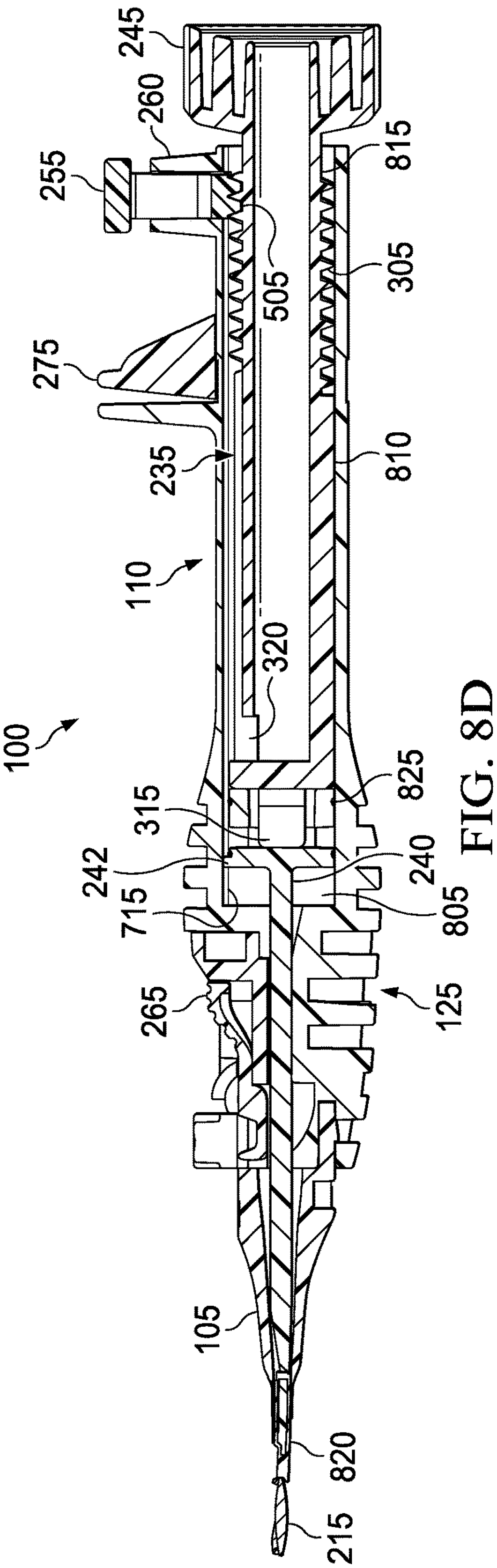

In the fourth state of the apparatus illustrated in FIG. 8D, the push rod 235 has been rotated to advance the push rod 235 axially from the position of FIG. 8C. For example, the finger grip 245 may be rotated, causing the threads 305 to engage the thread tracks 505 to control advancement of the push rod 235, and thereby controlling advancement of the plunger 240. For example, the plunger interface 315 may rotate within the head 825 while the plunger track 715 and the lug 242 can prevent rotation of the plunger 240 as the push rod 235 is twisted to advance the plunger 240 and the implant 215 until the implant 215 is ejected from the nozzle 105.

Figure 8E:
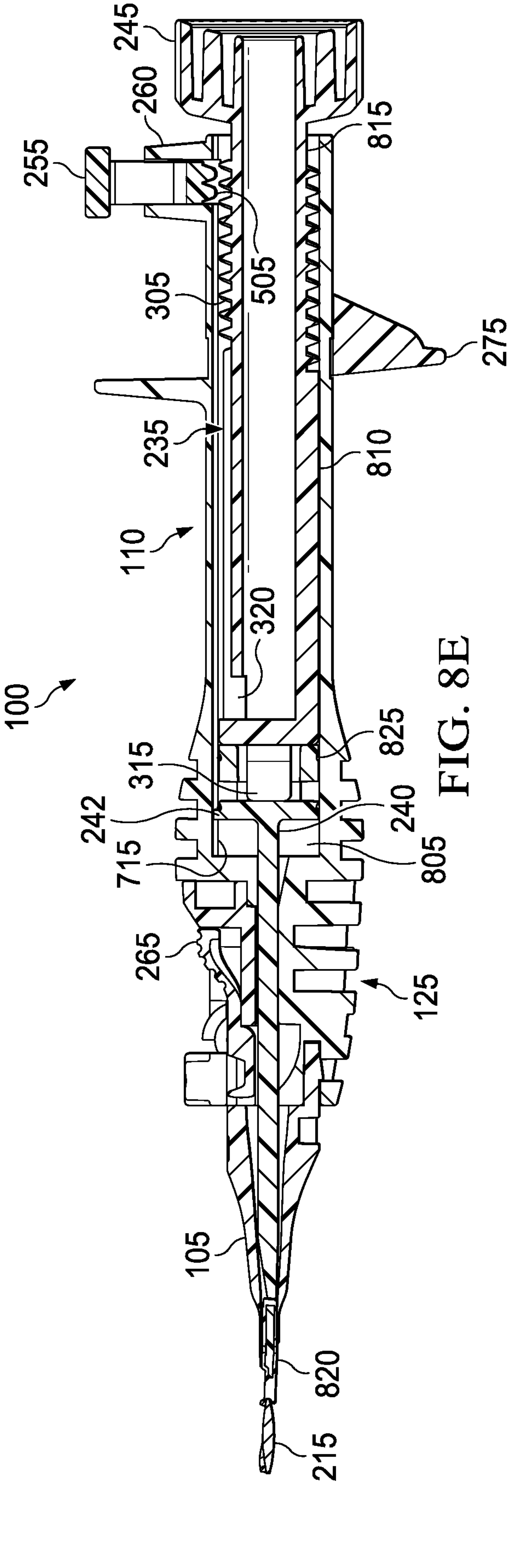

FIG. 8E illustrates a fifth state of the apparatus 100. The fifth state of FIG. 8E represents an alternative to the fourth state illustrated in FIG. 8D. More particularly, in the fifth state of FIG. 8E, the plunger key 255 has been moved from the second key position illustrated in FIG. 8C, to a third key position, corresponding substantially to the position illustrated in FIG. 7C. In this third key position, the thread tracks 505 are disengaged or otherwise removed from the threads 305, thereby allowing advancement of the push rod 235 by axial loads rather than the rotational advancement illustrated in the fourth state of FIG. 8D. In the example of FIG. 8E, the push rod 235 has been advanced from the position of FIG. 8C, thereby advancing the plunger 240 and the implant 215. For example, the finger grip 245 may be pushed to control advancement of the push rod 235, thereby controlling advancement of the plunger 240 and the implant 215 until the implant 215 is ejected from the nozzle 105. In some embodiments, the second finger flange 275 may be rotated down to facilitate use of a single hand to advance the push rod 235.

Figure 9:
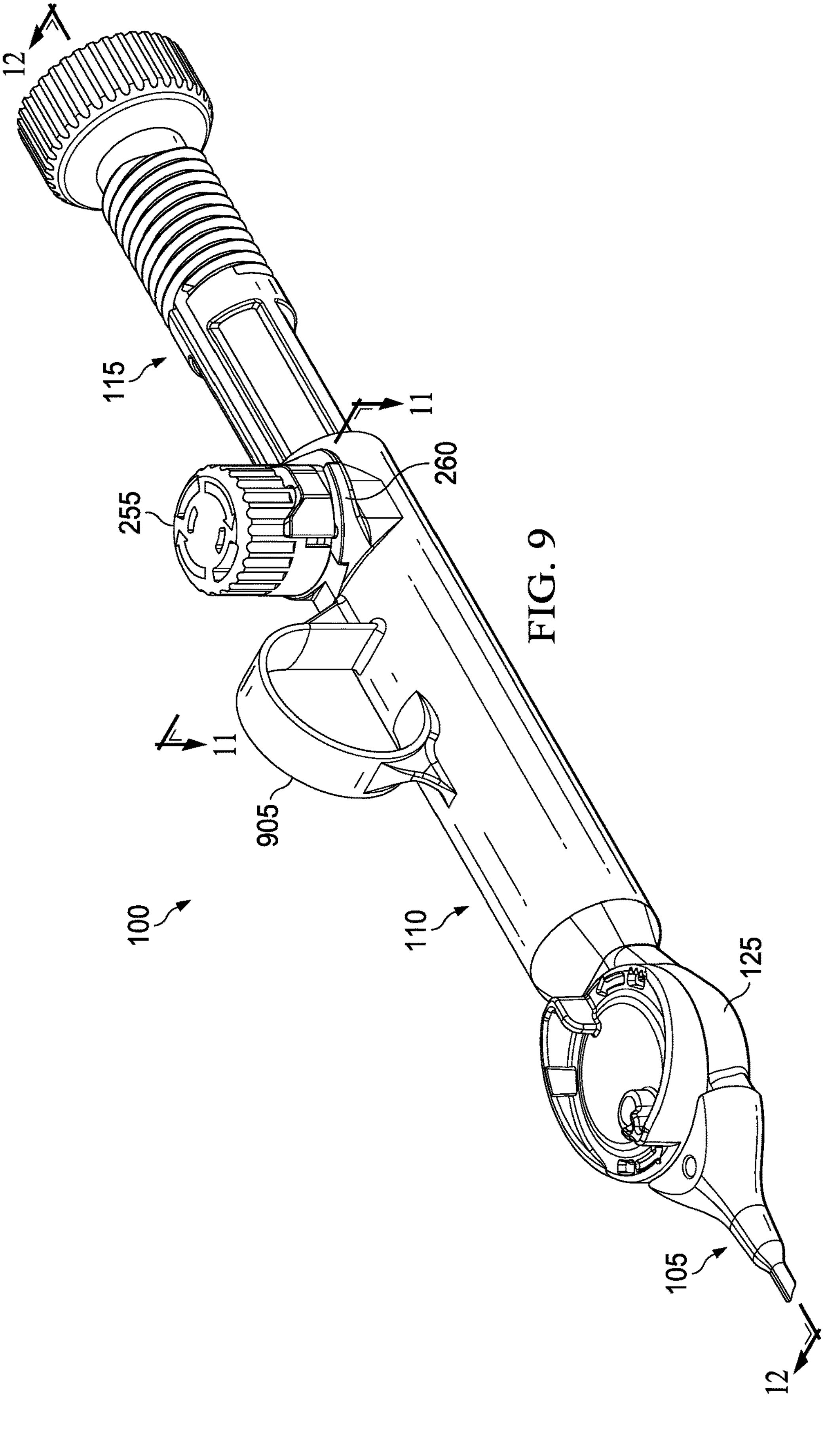
FIG. 9 is an auxiliary view of another example apparatus for delivering an implant into an eye.

FIG. 9 is an isometric view of another example of the apparatus 100. The apparatus 100 of FIG. 9 shares several features with previous examples. For example, the apparatus 100 of FIG. 9 may include the nozzle 105, the housing 110, and the actuator 115. As in FIG. 1, the housing 110 may be coupled to the nozzle 105, and the housing 110 is generally configured to receive at least a portion of the actuator 115. The housing 110 may further comprise the implant bay 125 and a finger loop 905. FIG. 9 also illustrates another example of the plunger key 255 and the key mount 260.

Figure 10:
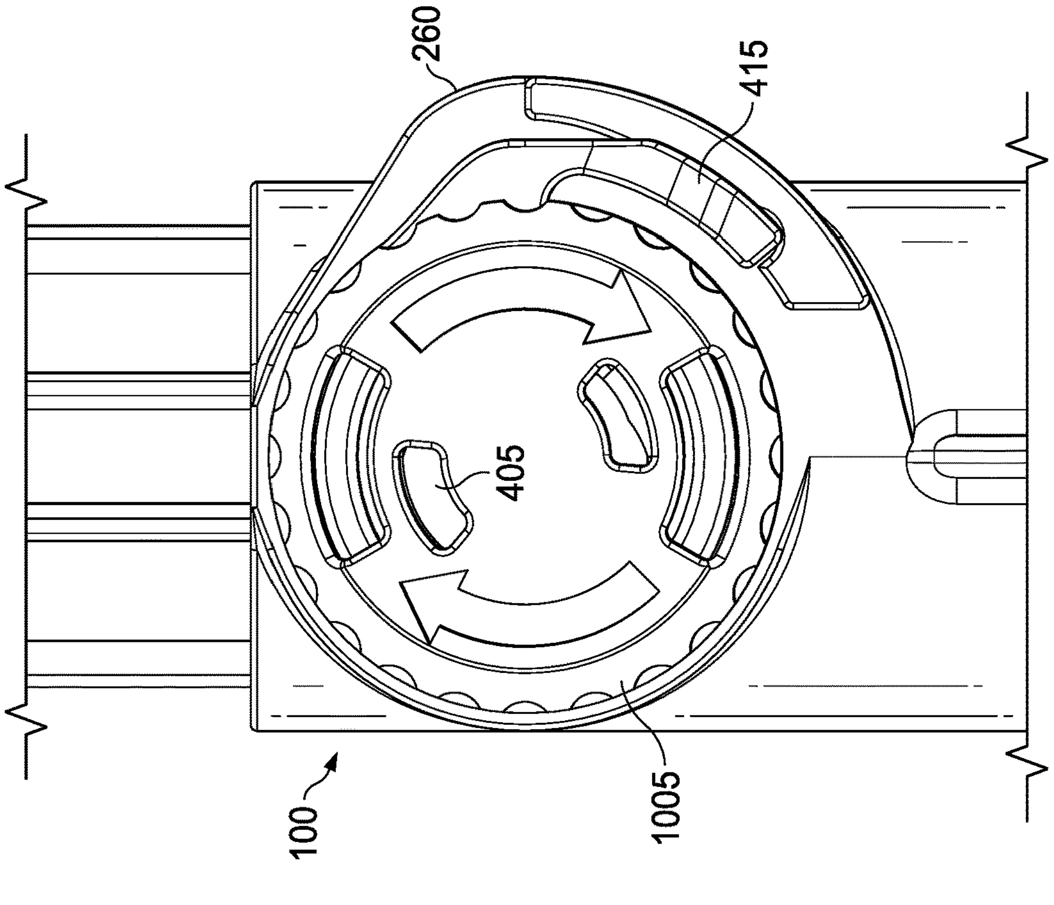
FIG. 10 is a partial top view of the apparatus of FIG. 9.

FIG. 10 is a partial top view of the apparatus 100 of FIG. 9, illustrating additional details that may be associated with some embodiments. For example, the plunger key 255 of FIG. 10 comprises a cap 1005, and one or more snap fittings 415 may be coupled indirectly to the shank 405 through the cap 1005. The cap 1005 may be disposed over other features of the plunger key 255, as well as over portions of the key mount 260. For example, the cap 1005 may be disposed over the shank 405 and the key track 710 in some examples.

Figure 11:
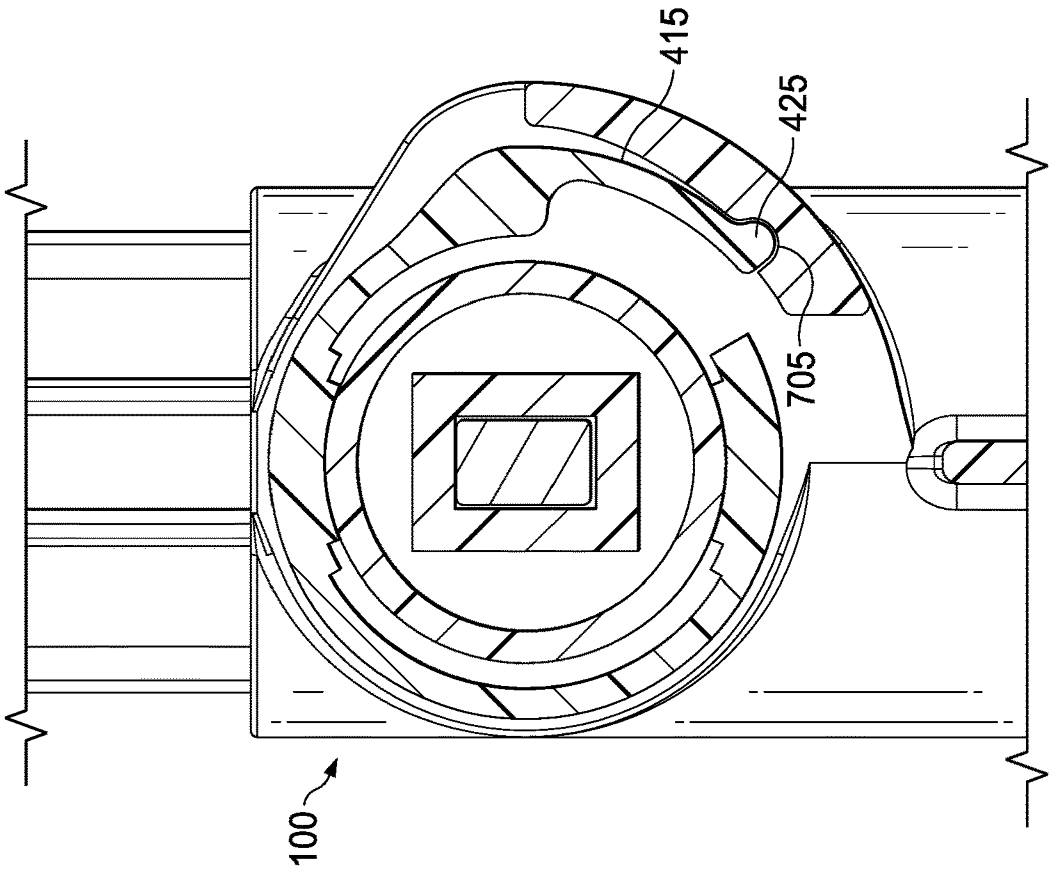
FIG. 11 is a partial top section view of the apparatus of FIG. 9.

FIG. 11 is a partial top section view of the apparatus 100 of FIG. 9, taken along line 11-11, illustrating additional details that may be associated with some embodiments. For example, FIG. 11 illustrates other examples of the lugs 425 and the catch 705. As illustrated, one or more of the lugs 425 may be coupled to the snap fitting 415 of FIG. 11. The catch 705 of FIG. 11 can engage the lug 425 to resist or prevent rotation of the cap 1005. The snap fitting 415 may be pressed toward the shank 405 to release the lug 425 from the catch 705, allowing the cap 1005 to be rotated until the catch 705 engages the lug 425 again after a complete rotation.

Figure 12:
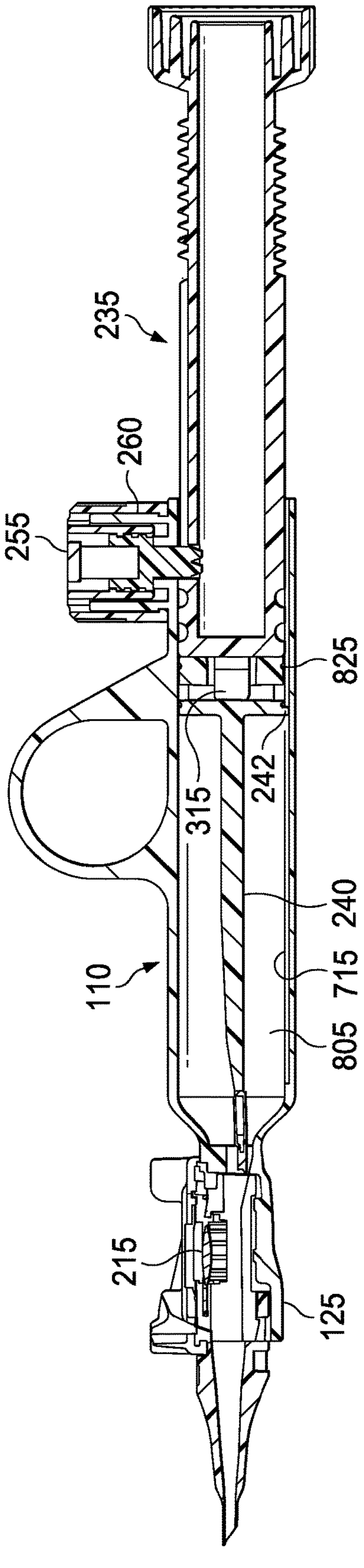
FIG. 12 is a section view of the apparatus of FIG. 9.

FIG. 12 is a section view of the apparatus of FIG. 9, taken along line 12-12, illustrating additional details that may be associated with some embodiments. FIG. 12 generally illustrates the housing 110 and the bore 805 through the housing 110. The push rod 235 may be at least partially disposed in the bore 805. The plunger 240 may also be disposed within the bore 805. The head 825 of the plunger 240 may be coupled to the push rod 235. In some examples, the head 825 may be coupled to the plunger interface 315. In some embodiments, the plunger 240 may also be coupled to the housing 110 to control rotational movement of the plunger 240. For example, the lug 242 can engage the plunger track 715, which can allow the push rod 235 to advance the plunger 240 axially while preventing rotation of the plunger 240 within the bore 805. The plunger key 255 may be coupled to the key mount 260. In the example of FIG. 12, the implant 215 is disposed in the implant bay 125.

Figure 13A:
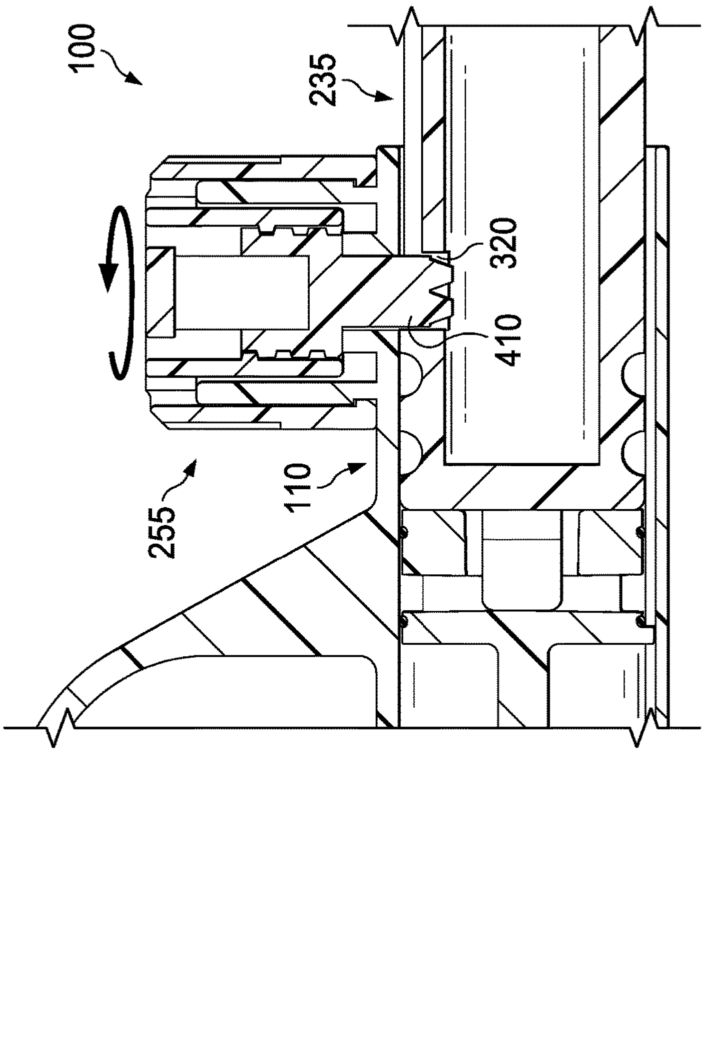
FIGS. 13A-13C are detail views of a portion of the apparatus of FIG. 12 in different states.

FIG. 13A is a detail view of a portion of the apparatus 100 of FIG. 12, illustrating additional details that may be associated with some embodiments. FIG. 13A illustrates the apparatus 100 with the plunger key 255 in a first state. In this state, the tip 410 of the plunger key 255 is in a first position, disposed in the keyway 320, which can prevent movement of the push rod 235. This state may be advantageous for transporting and storing the apparatus 100, for example.

Figure 13B:
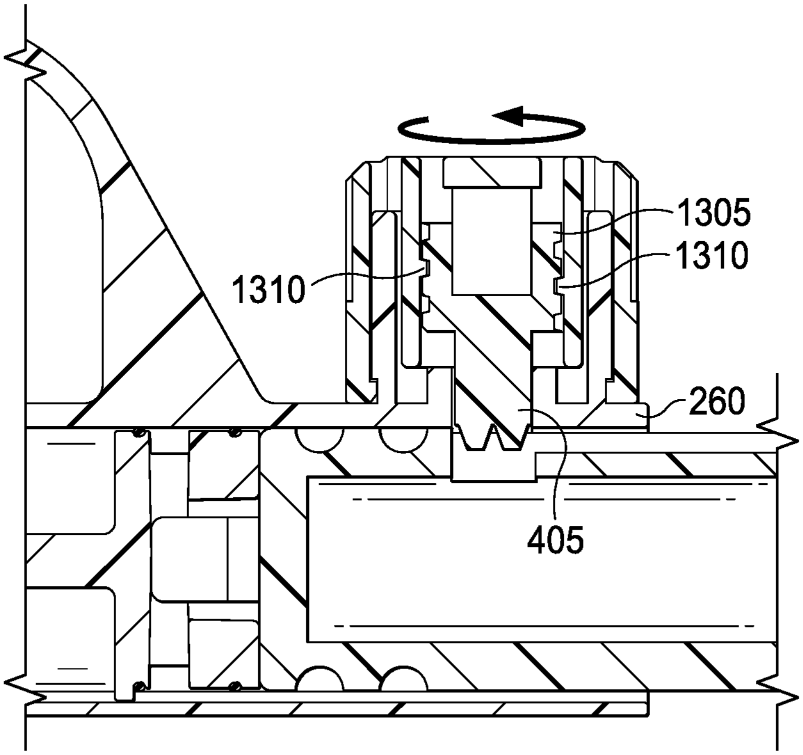

FIG. 13B illustrates the plunger key 255 of FIG. 13A in a second state. For example, the snap fitting 415 (not shown in FIG. 13B) may be pressed toward the shank 405 to release the lug 425 (not shown in FIG. 13B) from the catch 705 (not shown in FIG. 13B), substantially as described with reference to FIG. 11. The cap 1005 of FIG. 13B is rotatable about the shank 405. The cap 1005 may also be coupled to the housing 110 to maintain its axial position during rotation. For example, the cap 1005 may engage the housing 110 through a cylindric clearance mating surface and a snap-in protrusion ring. The ring can maintain the axial position of the cap 1005 whiling it's rotating to drive the plunger key 255 from one position to another. Rotating the cap 1005 can remove the tip 410 from the keyway 320. For example, the shank 405 may have external threads 1305 and the cap 1005 may have internal thread tracks 1310 configured to engage the threads 1305. The key mount 260 may prevent rotation of the shank 405, so that rotation of the cap 1005 causes the thread tracks 1310 to slide through the threads 1305, thereby moving the shank 405 relative to the push rod 235. For example, rotating the cap 1005 one full turn until the catch 705 re-engages the lug 425 can move the tip 410 from the first position of FIG. 13A to a second position, as illustrated in FIG. 13B.

Figure 13C:
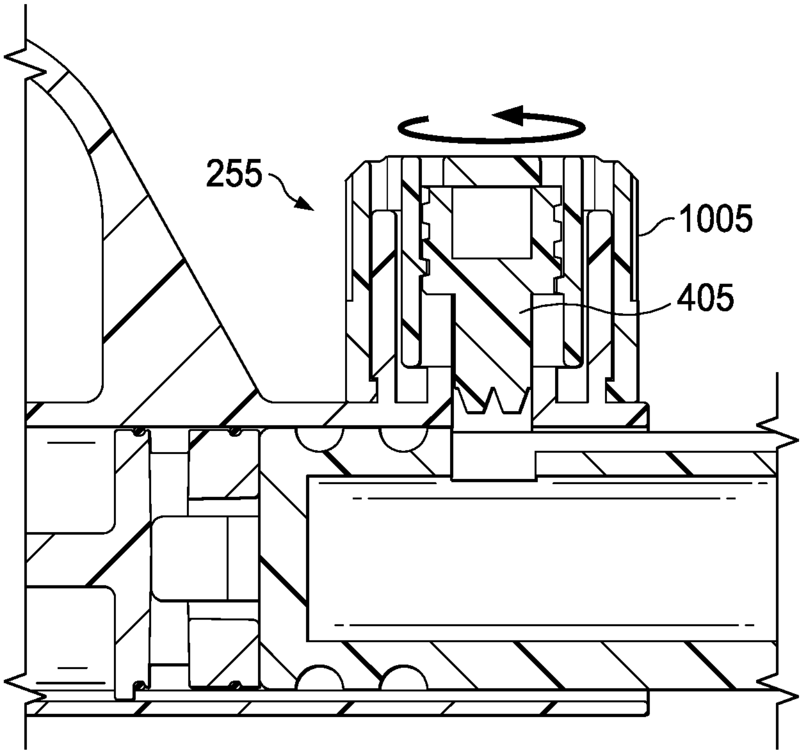

FIG. 13C illustrates the plunger key 255 of FIG. 13A in a third state. In the third state of FIG. 13C, for example, the cap 1005 can be rotated another full turn, thereby further retracting the shank 405 within the cap 1005 from the second position of FIG. 13B to a third position.

Accordingly, the plunger key 255 can be manipulated between a first position, a second position, and a third position, analogous or similar to the positions illustrated above with respect to FIG. 7A, FIG. 7B, and FIG. 7C. Likewise, the push rod 235 can be operated substantially as described with reference to FIGS. 8A-8E to eject an implant.

Figure 14A:
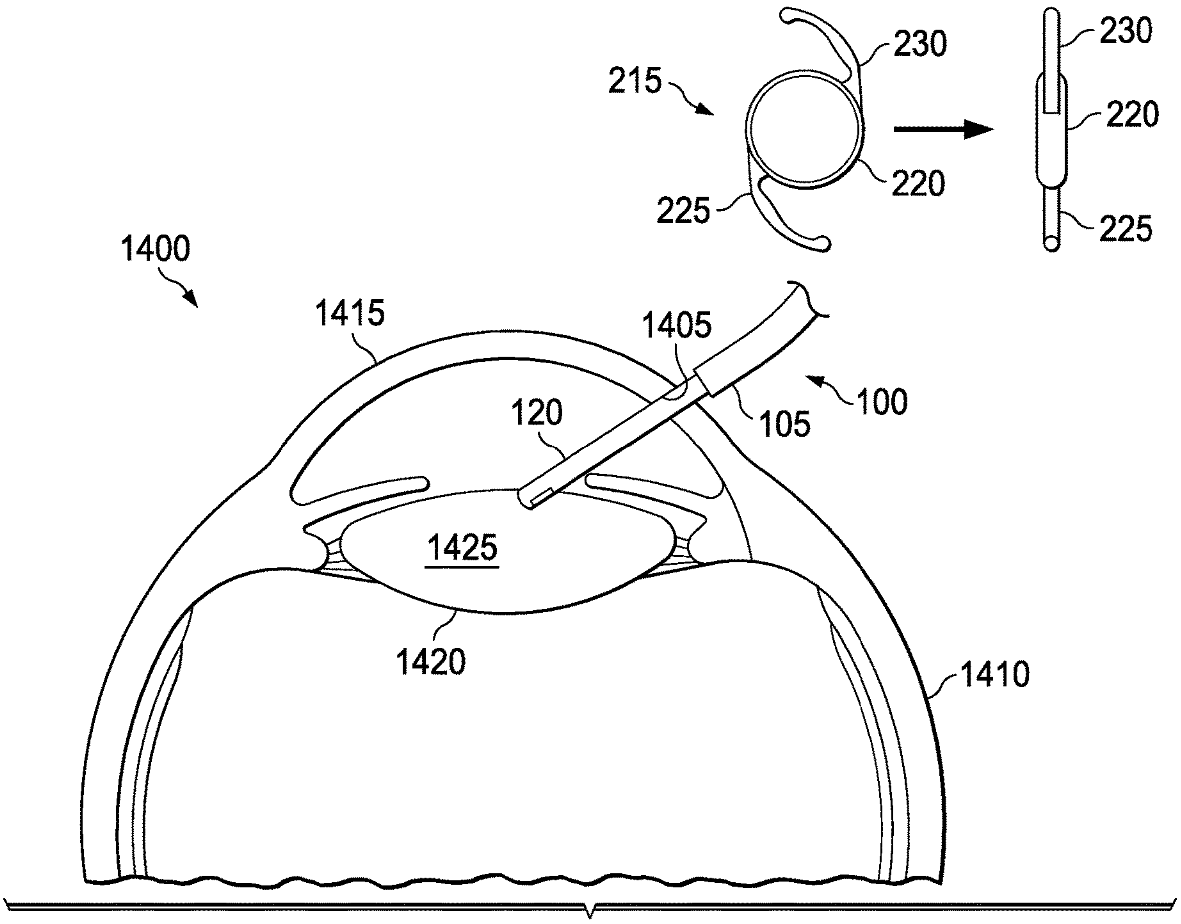
FIG. 14A and FIG. 14B are schematic diagrams illustrating an example use of the apparatus of FIG. 1 or FIG. 9 to deliver an implant to an eye.
Figure 14B:
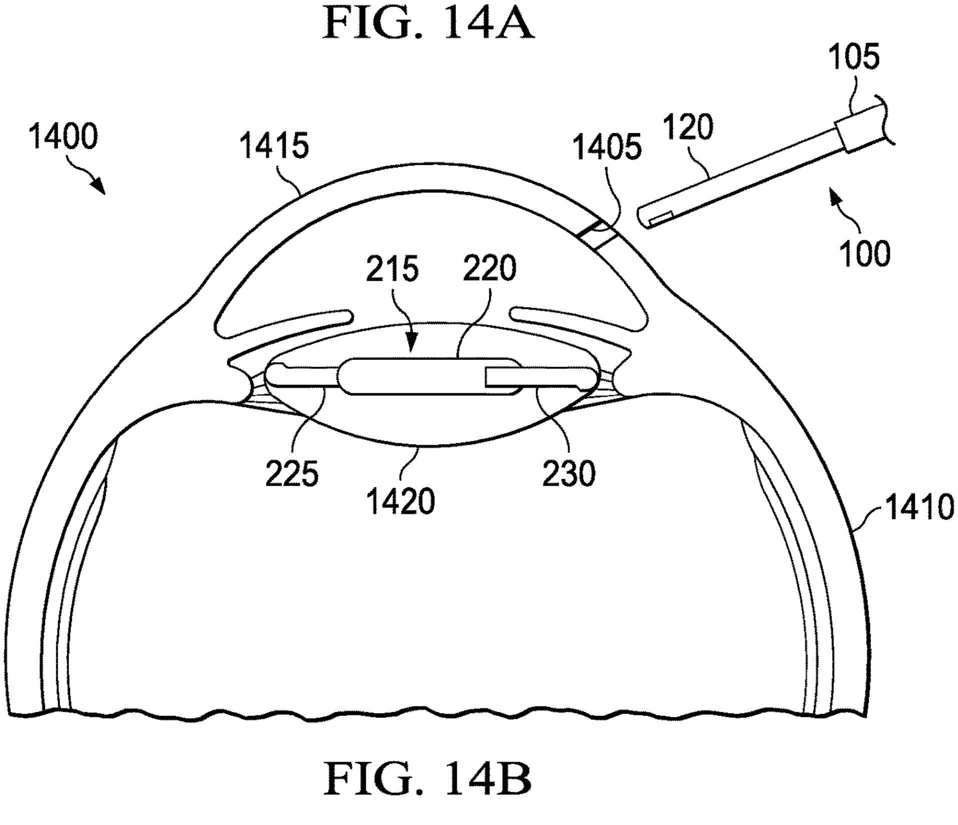

FIG. 14A and FIG. 14B are schematic diagrams illustrating an example use of the apparatus 100 to deliver the implant 215 to an eye 1400. As illustrated, an incision 1405 may be made in the eye 1400 by a surgeon, for example. In some instances, the incision 1405 may be made through the sclera 1410 of the eye 1400. In other instances, an incision may be formed in the cornea 1415 of the eye 1400. The incision 1405 may be sized to permit insertion of a portion of the nozzle 105 to deliver the implant 215 into the capsular bag 1420. For example, in some instances, the size of the incision 1405 may have a length less than about 3000 microns (3 millimeters). In other instances, the incision 1405 may have a length of from about 1000 microns to about 1500 microns, from about 1500 microns to about 2000 microns, from about 2000 microns to about 2500 microns, or from about 2500 microns to about 3000 microns.

After the incision 1405 is made, the nozzle 105 can be inserted through the incision 1405 so that the width of the tip 120 aligns with the length of the incision 1405, allowing the nozzle 105 to extend into an interior portion 1425 of the eye 1400. The apparatus 100 can then eject the implant 215 through the nozzle 105 into the capsular bag 1420 of the eye 1400, substantially as described with reference to FIGS. 8A-8E or FIGS. 13A-13C.

In some embodiments, the implant 215 may comprise an intraocular lens having a shape similar to that of a natural lens of an eye, and it may be made from numerous materials. Examples of suitable materials may include silicone, acrylic, and combinations of such suitable materials. In some instances, the implant 215 may comprise an intraocular lens that is fluid-filled, such as a fluid-filled accommodating intraocular lens. The implant 215 may also comprise an intraocular lens that includes one or more features, such as haptics, for positioning the intraocular lens within an eye. In the example of FIG. 14A and FIG. 14B, the implant 215 is illustrative of an intraocular lens having an optic body 220, a leading haptic 225, and a trailing haptic 230.

The implant 215 may be delivered in a folded configuration and can revert to a resting state with the leading haptic 225 and the trailing haptic 230 being at least partially curved around the optic body 220, within the capsular bag 1420, as shown in FIG. 14B. The capsular bag 1420 can retain the implant 215 within the capsular bag 1420 in a relationship relative to the eye 1400 so that the optic body 220 refracts light directed to the retina (not shown). The leading haptic 225 and the trailing haptic 230 can engage the capsular bag 1420 to secure the implant 215 therein. After delivering the implant 215 into the capsular bag 1420, the nozzle 105 may be removed from the eye 1400 through the incision 1405, and the eye 1400 can be allowed to heal over time.

The systems, apparatuses, and methods described herein may provide significant advantages. Some embodiments may be particularly advantageous for delivering intraocular lenses, providing multiple delivery modes in a single apparatus. For example, some embodiments of the apparatus 100 may provide a choice of single-handed push delivery or two-handed push and twist delivery, so that a surgeon may select a delivery mode based upon preference or other conditions.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may also be combined or eliminated in various configurations for purposes of sale, manufacture, assembly, or use. For example, in some configurations, the nozzle 105, the implant bay 125, and the actuator 115 may each be separated from one another or combined in various ways for manufacture or sale.

The claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for eye surgery, the apparatus comprising:
a housing;
a bore through the housing;
a push rod at least partially disposed in the bore and operable to move from a first rod position to a second rod position and a third rod position within the bore; and
a plunger key coupled to the housing and operable to move between a first key position, a second key position, and a third key position;
wherein the plunger key in the first key position prevents the push rod from moving from the first rod position, in the second key position allows the push rod to slide through the bore from the first rod position to the second rod position and to rotate from the second rod position to the third rod position, and in the third key position allows the push rod to slide through the bore from the second rod position to the third rod position.

2. The apparatus of claim 1, wherein:
the push rod comprises threads; and
the plunger key comprises one or more thread tracks, the thread tracks configured to mate with the threads of the push rod so that the push rod may be rotated to advance from the second rod position to the third rod position if the plunger key is in the second key position.

3. The apparatus of claim 2, wherein:
the push rod further comprises a slide track; and
the plunger key is configured to slidingly engage the slide track if the plunger key is in the second key position and the push rod is between the first rod position and the second rod position.

4. The apparatus of claim 2, wherein the push rod further comprises a slide track configured to stop the push rod at the second position.

5. The apparatus of claim 1, wherein the push rod further comprises a keyway configured to receive a portion of the plunger key in the first rod position and the first key position.

6. The apparatus of claim 1, wherein the housing comprises a key mount configured to retain the plunger key in each of the first key position, the second key position, and the third key position.

7. The apparatus of claim 6, wherein the plunger key comprises:
a shank;
a tip coupled to one end of the shank; and
one or more snap fittings coupled to the shank;
wherein the snap fittings are configured to engage the key mount in each of the first key position, the second key position, and the third key position.

8. The apparatus of claim 6, wherein the key mount comprises a catch configured to engage the plunger key in each of the first key position, the second key position, and the third key position.

9. The apparatus of claim 8, wherein the plunger key comprises:
a shank;
one or more snap fittings coupled to the shank; and
one or more lugs coupled to the snap fittings;
wherein the lugs are configured to engage the catch in each of the first key position, the second key position, and the third key position.

10. The apparatus of claim 8, wherein the plunger key comprises:
a shank;
a cap disposed over the shank;
one or more snap fittings coupled to the cap; and
one or more lugs coupled to the snap fittings;
wherein the lugs are configured to engage the catch in each of the first key position, the second key position, and the third key position.

11. The apparatus of claim 10, wherein the cap is rotatable about the shank to move the plunger key between the first key position, the second key position, and the third key position.

12. The apparatus of claim 11, wherein:
the shank comprises external threads; and
the cap comprises internal thread tracks configured to engage the external threads of the shank to move the plunger key.

13. The apparatus of claim 1, further comprising:
a nozzle;
an implant bay coupled to the nozzle;
an implant disposed within the implant bay; and
a plunger coupled to the push rod in the bore;
wherein the push rod is configured to advance the plunger to advance the implant through the nozzle as the push rod moves to the third rod position.

14. An apparatus for eye surgery, the apparatus comprising:
a housing;
a key mount coupled to the housing, the key mount comprising a key track and a catch;
a bore through the housing;
a plunger disposed in the bore;
a push rod coupled to the plunger and operable to move from a first rod position to a second rod position and a third rod position within the bore, the push rod comprising:
a keyway,
a slide track, and
threads; and
a plunger key, the plunger key comprising:
a shank disposed within the key track,
a tip coupled to one end of the shank, the tip having one or more thread tracks,
a snap fitting coupled to the shank, and
a lug coupled to the snap fitting;
wherein:
the shank is operable to move the tip from a first key position to a second key position and a third key position, and the lug is configured to engage the catch in each of the first key position, the second key position, and the third key position,
in the first key position, the tip is disposed in the keyway,
in the second key position, the tip is configured to engage the slide track between the first rod position and the second rod position, and
in the second key position, the thread tracks are configured to engage the threads.

15. An apparatus for delivering an implant to an eye, the apparatus comprising:
a nozzle;
an implant bay coupled to the nozzle;
an implant disposed in the implant bay;
a housing;
a bore through the housing;
an actuator, the actuator comprising:
a plunger disposed within the bore, and
a push rod at least partially disposed in the bore and operable to move the plunger from a first plunger position to a second plunger position and a third plunger position within the bore; and
a plunger key coupled to the housing and operable to move between a first key position, a second key position, and a third key position;
wherein the plunger key in the first key position prevents the push rod from moving the plunger from the first plunger position, in the second key position allows the push rod to slide the plunger through the bore from the first plunger position to the second plunger position and to rotate to move the plunger to the third plunger position to advance the implant from the implant bay through the nozzle, and in the third key position allows the push rod to slide the plunger through the bore from the second plunger position to the third plunger position to advance the implant from the implant bay through the nozzle.

* * * * *